United States Patent
Gossling et al.

(10) Patent No.: US 11,327,529 B2
(45) Date of Patent: May 10, 2022

(54) SENSOR APPARATUS

(71) Applicant: 270 VISION LTD, Hedge End (GB)

(72) Inventors: Martin Gossling, Chibolton (GB); Nick Belson, Chibolton (GB)

(73) Assignee: 270 VISION LTD, Hedge End (GB)

( * ) Notice: Subject to any disclaimer, the term of this patent is extended or adjusted under 35 U.S.C. 154(b) by 0 days.

(21) Appl. No.: 17/042,324

(22) PCT Filed: Mar. 28, 2019

(86) PCT No.: PCT/GB2019/050901
§ 371 (c)(1),
(2) Date: Sep. 28, 2020

(87) PCT Pub. No.: WO2019/186179
PCT Pub. Date: Oct. 3, 2019

(65) Prior Publication Data
US 2021/0011509 A1    Jan. 14, 2021

(30) Foreign Application Priority Data
Mar. 29, 2018   (GB) ..................................... 1805186

(51) Int. Cl.
*G08B 21/00*        (2006.01)
*G06F 1/16*         (2006.01)
(Continued)

(52) U.S. Cl.
CPC ............. *G06F 1/163* (2013.01); *A41D 1/002* (2013.01); *A61B 5/11* (2013.01); *A61B 5/6804* (2013.01);
(Continued)

(58) Field of Classification Search
CPC ....... G06F 1/163; G06F 1/1694; A41D 1/002; A61B 5/11; A61B 5/6804; A61B 2562/0219
(Continued)

(56) References Cited

U.S. PATENT DOCUMENTS 9,571,723 B2 *  2/2017  Velipasalar ..........  A61B 5/7264
9,666,052 B1    5/2017  Smith
(Continued)

FOREIGN PATENT DOCUMENTS

EP          3 416 146 A1    12/2018

OTHER PUBLICATIONS

Combined Search and Examination Report for Great Britain Application No. GB1805186.2, dated Oct. 2, 2018.
(Continued)

*Primary Examiner* — Zhen Y Wu
(74) *Attorney, Agent, or Firm* — Barnes & Thornburg LLP (57) ABSTRACT

A sensor apparatus for an item of smart clothing is disclosed herein. The sensor apparatus houses sensor electronics comprising at least one position and/or orientation sensor, and a data store, coupled to a processor and powered by a battery. The processor is configured to receive signals indicative of a change in position and/or orientation from the at least one position and/or orientation sensor. The processor is also configured to determine from the received signals whether there has been a change in position and/or orientation of the sensor apparatus over a first selected time interval; and in the event that there has been a change in position and/or orientation of the sensor apparatus over the first selected time interval, the processor is configured to record the change in position and/or orientation to the data store.

14 Claims, 4 Drawing Sheets

(51) Int. Cl.
*A41D 1/00* (2018.01)
*A61B 5/11* (2006.01)
*A61B 5/00* (2006.01)

(52) U.S. Cl.
CPC .... *G06F 1/1694* (2013.01); *A61B 2562/0219* (2013.01)

(58) Field of Classification Search
USPC .......................................................... 340/669
See application file for complete search history.

(56) References Cited

U.S. PATENT DOCUMENTS

| | | | |
|---|---|---|---|
| 2002/0008630 A1 | 1/2002 | Lehrman et al. | |
| 2008/0164979 A1* | 7/2008 | Otto | A61B 5/0024 340/286.01 |
| 2010/0145236 A1 | 6/2010 | Greenberg et al. | |
| 2011/0087115 A1 | 4/2011 | Sackner et al. | |
| 2011/0263950 A1* | 10/2011 | Larson | G16H 20/00 600/301 |
| 2012/0314901 A1* | 12/2012 | Hanson | G08B 21/02 382/103 |
| 2013/0181831 A1 | 7/2013 | Liu | |
| 2014/0070957 A1* | 3/2014 | Longinotti-Buitoni | G06F 3/011 340/870.01 |
| 2015/0375042 A1* | 12/2015 | Schaffer | A61B 5/0004 482/8 |
| 2016/0042726 A1* | 2/2016 | Glaser | G01N 25/56 705/4 |
| 2016/0180440 A1* | 6/2016 | Dibenedetto | A61B 5/112 705/26.7 |
| 2016/0203692 A1* | 7/2016 | Ten Kate | A61B 5/681 340/573.1 |
| 2016/0245665 A1* | 8/2016 | Logan | G01W 1/00 |
| 2016/0287937 A1 | 10/2016 | Fitzgerald et al. | |
| 2017/0171290 A1* | 6/2017 | Bhardwaj | G06F 40/169 |
| 2017/0245806 A1* | 8/2017 | Elhawary | A61B 5/681 |
| 2017/0315821 A1* | 11/2017 | Hayes | G06F 1/3287 |
| 2017/0360357 A1 | 12/2017 | Larson et al. | |
| 2018/0000385 A1* | 1/2018 | Heaton | G08B 21/0446 |
| 2018/0064388 A1* | 3/2018 | Heneghan | A61B 5/11 |
| 2018/0070840 A1* | 3/2018 | Cronin | A61B 5/6824 |
| 2018/0167499 A1* | 6/2018 | Torvinen | H04M 1/72409 |
| 2019/0069243 A1* | 2/2019 | Bean | G06F 1/28 |
| 2019/0138068 A1* | 5/2019 | Park | G06F 1/163 |
| 2020/0281536 A1* | 9/2020 | Ljung | A61B 5/7246 |

OTHER PUBLICATIONS

Search Report (1) for Great Britain Application No. GB1805186.2, dated Feb. 5, 2019.
Search Report (2) for Great Britain Application No. GB1805186.2, dated Feb. 5, 2019.
Search Report (3) for Great Britain Application No. GB1805186.2, dated Feb. 5, 2019.
Search Report & Written Opinion issued in Int'l Appl. No. PCT/GB2019/050901, dated Aug. 22, 2019.

* cited by examiner

SENSOR APPARATUS

This application is a U.S. national stage application under 35 USC § 371 of PCT Application No. PCT/GB2019/050901, filed on Mar. 28, 2019, which claims priority from United Kingdom Application No. GB 1805186.2, filed on Mar. 29, 2018, the entirety of which are both hereby fully incorporated by reference herein.

FIELD OF THE INVENTION

The present disclosure relates to a sensor apparatus comprising at least one position and/or orientation sensor.

BACKGROUND

The "internet of things" is an increasing trend, and there is a desire for items of "smart clothing" that incorporate battery-powered sensors. Items of "smart clothing" may allow various parameters of the user wearing the item of smart clothing to be measured and monitored by use of the incorporated sensors. In some cases, the sensors may be permanently fixed to the item of smart clothing. If this is the case then the sensors must be rugged enough for them to be in place whilst the garment is washed and dried, which means the apparatus they are in has to prevent both mechanical damage and to be waterproof, which negates the use of connectors. In addition, there may be multiple sensors incorporated into the item of clothing, making separate charging of each one inconvenient. Wiring them all up together is also sometimes impractical.

SUMMARY OF THE INVENTION

Aspects of the invention are as set out in the independent claims and optional features are set out in the dependent claims. Aspects of the invention may be provided in conjunction with each other and features of one aspect may be applied to other aspects.

In an aspect of the disclosure there is described a sensor apparatus for an item of smart clothing, the sensor apparatus comprising sensor electronics comprising at least one position and/or orientation sensor, and a data store, coupled to a processor and powered by a battery;
  wherein the processor is configured to receive signals indicative of a change in position and/or orientation from the at least one position and/or orientation sensor;
  wherein the processor is configured to determine from the received signals whether there has been a change in position and/or orientation of the sensor apparatus over a first selected time interval; and
  in the event that there has been a change in position and/or orientation of the sensor apparatus over the first selected time interval, the processor is configured to record the change in position and/or orientation to the data store.

Because the processor is configured to only record the change in position and/or orientation if there has been a change, the amount of data that needs to be recorded can be reduced. This in turn means that the amount of data that needs to be uploaded from the sensor to a remote device, such as a server, that processes the sensor data, is reduced. By such "intelligent monitoring" of the data being produced at the "Edge" of the complete network, it enables analytics to be performed close to the source of the data. This has the advantage as it reduces latency because data does not have to traverse over a network to a data centre or cloud for processing. It also reduces the data set transferred so reduce bandwidth requirements and price per byte costs.

Although the sensors are described as battery-powered sensors, it will be understood that in some examples the sensors may not comprise batteries but may instead be powered by some other form of electrical energy storage, for example a capacitive form of energy storage. It will also be understood that the term battery may encompass a single electrochemical cell and/or a plurality of cells.

The at least one position and/or orientation sensor may be at least one of: a 3-axis accelerometer, a 3-axis gyroscope and a magnetometer.

In some examples, in the event that there has not been a change in position and/or orientation of the sensor apparatus over the first selected time interval, the processor is configured to record a null or no value to the data store. This may reduce the size of the data store required to capture data over a day's use of the sensor apparatus.

The processor may be configured to determine if the position and/or orientation of the sensor apparatus is still changing at the end of the selected time interval, and in the event that the position and/or orientation of the sensor apparatus has stopped changing at the end of the first selected time interval, to record the change in position and/or orientation to the data store.

In some examples, in the event that the position and/or orientation of the sensor apparatus is still changing at the end of the first selected time interval, the processor is configured to record a null or no value to the data store. This may reduce the size of the data store required to capture data over a day's use of the sensor apparatus.

Recording the change in position and/or orientation may comprise recording the position and/or orientation of the sensor apparatus at the beginning of the first selected time interval and the position and/or orientation of the sensor apparatus at the end of the selected time interval.

The processor may be configured to record the change in position and/or orientation to the data store in the event that the change in position and/or orientation is above a threshold level of change in position and/or orientation. For example, the processor may be configured to record the change in position and/or orientation to the data store in the event that the change in orientation is greater than 10 degrees, greater than 20 degrees, greater than 30 degrees.

The processor may be configured to receive signals from the at least one position and/or orientation sensor by polling the position and/or orientation sensor repeatedly at a second selected time interval that is shorter than the first selected time interval for determining if there has been a change in position and/or orientation of the sensor apparatus.

In some examples the processor comprises a system clock and wherein the processor is configured to record a time based on the system clock when recording a change in position and/or orientation.

The processor may be coupled to and configured to operate a wireless communications interface, and wherein the processor is configured to upload data stored in the data store to a remote device via the wireless communications interface. In some examples the wireless interface comprises a Bluetooth LE v4.2 or above module.

The processor may be configured to determine if the wireless communications interface is coupled to the remote device and in response to determining that the wireless communications interface is coupled to the remote device, upload data stored in the data store to the remote device.

In some examples the sensor apparatus comprises a wireless charging interface for wirelessly charging the battery, and wherein the processor is configured to determine if the battery is being charged via the wireless charging interface, and in response to determining that the battery is being charged via the wireless charging interface, upload data stored in the data store to the remote device via the wireless communications interface.

The charging interface may be configured to receive a charging current from a remote charging station via the wireless charging interface, and wherein the processor is configured to synchronise the system clock to a time signal received from the remote charging station via the wireless communications interface.

The processor may be configured to operate the wireless communications interface to communicate with the wireless communications interface of another sensor apparatus, and to receive signals indicative of a change in position and/or orientation from at least one position and/or orientation sensor from the other sensor apparatus and to determine the position and/or orientation of the other sensor apparatus, and compare the position and/or orientation of the other sensor apparatus with its own position and/or orientation.

The processor may be configured to determine whether there has been a change in position and/or orientation of the other sensor apparatus with respect to the sensor over a third selected time interval; and
   in the event that there has been a change in position and/or orientation of the other sensor apparatus over the third selected time interval, the processor is configured to record the change in position and/or orientation of the other sensor apparatus to the data store.

In some examples the processor is shared with at least one of the wireless communications interface and the wireless charging interface.

In another aspect there is provided a sensor apparatus for an item of smart clothing, the sensor apparatus comprising sensor electronics comprising at least one position and/or orientation sensor, a wireless communications interface and a data store, coupled to a processor and powered by a battery;
   wherein the processor is configured to receive signals indicative of a change in position and/or orientation from the at least one position and/or orientation sensor and record data based on the received signals to the data store;
   wherein the processor is configured to determine if the wireless communications interface is coupled to a remote device and in response to determining that the wireless communications interface is coupled to the remote device, upload data to the remote device; and
   wherein the processor is configured to adjust the data uploaded to the remote device based on at least one of
   (i) an analysis of the data stored on the data store and
   (ii) a parameter of the connection with the remote device via the wireless communications interface.

The analysis performed by the processor may comprise determining if the data can be compressed, or if the volume of data can be reduced. For example, the processor may be configured to remove data values where there has been no change in position and/or orientation, or only a change in positions and/or orientation below a selected threshold level.

The parameter of the connection with the remote device may comprise at least one of the bandwidth of the connection with the remote device, and the battery level of the battery in the sensor apparatus. For example, if the bandwidth is low, the processor may be configured to send less data to the remote device. Similarly, if the battery level is low (for example below a selected threshold) the processor may be configured to send less data to the remote device. The remote device may be based on the cloud (for example provided as a means of internet/web-based storage). The connection with the remote device may be direct, for example the sensor apparatus may connect directly to a wide area network such as the internet via the wireless communications interface, or it may be indirect, for example the sensor may connect to a user's mobile phone via the wireless communications interface, which in turn may connect to a wide area network such as the internet to connect to a remote device, such as the cloud.

In some examples the sensor apparatus further comprises at least one of a temperature sensor and a humidity sensor, and wherein the processor is configured to determine and record temperature and/or humidity data to the data store based on signals received from the at least one of a temperature sensor and a humidity sensor.

The processor may be configured to record temperature and/or humidity data to the data store when the processor records the change in position and/or orientation to the data store. Alternatively, the processor may be configured to record temperature and/or humidity data less frequently than the position/orientation data.

In some examples the processor is configured to send an alert via the wireless communications interface in the event that the determined temperature and/or humidity are above a selected threshold. For example, the processor may be configured to send the alert via a Bluetooth® broadcast channel. In some examples the alert may be configured to turn off "smart" equipment receptive to the alert, for example a "smart" tumble drier or washing machine which the sensor apparatus may have accidentally been placed inside.

The processor may be configured to determine a rate of increase in temperature and/or humidity, and is configured to send an alert via the wireless communications interface in the event that the determined rate of increase in temperature and/or humidity are above a selected threshold rate of increase.

In another aspect of the disclosure there is described a sensor apparatus for an item of smart clothing, the sensor apparatus comprising sensor electronics comprising:
   a position and/or orientation sensor coupled to a processor;
   a temperature and/or humidity sensor coupled to the processor;
   a wireless communications interface coupled to the processor; and
   a battery for powering the processor;
   wherein the processor is configured to determine at least one of a temperature and/or humidity based on signals received from the temperature and/or humidity sensor, and to send an alert via the wireless interface in the event that the determined temperature and/or humidity are above a selected threshold.

The processor may be configured to determine a rate of increase in temperature and/or humidity, and is configured to send an alert via the wireless communications interface in the event that the determined rate of increase in temperature and/or humidity are above a selected threshold rate of increase.

In some examples, in response to a signal received via the wireless interface, the processor is configured to disconnect sensors from the battery and to reduce the battery level below a selected level of charge, option wherein the selected level of charge is 25% or less of fully charged.

In some examples the sensor apparatus further comprises an isolator switch connected between the battery and the processor, and wherein in response to receiving an isolate signal via the wireless communications interface, the processor is configured to operate the isolate switch to disconnect the battery from at least some, for example all, of the sensor electronics. For example the isolate switch may be configured to disconnect the battery from at least one of the processor, the wireless communications interface, the at least one position and/or orientation sensor, the data store and if present a wireless charging interface (see discussion below).

In some examples the sensor apparatus further comprises a wireless charging interface for wirelessly charging the battery wherein the processor is configured to determine if the battery is being charged via the wireless charging interface, and in response to determining that the battery is being charged via the wireless charging interface, the processor is configured to operate the isolator switch to connect the battery to at least some of the sensor electronics. In some examples the processor may be configured to set a flag to keep the isolator switch on in response to determining that the battery is being charged via the wireless charging interface.

In some examples the sensor apparatus further comprises a fuse connected between the battery and the isolator switch, wherein the fuse is configured to blow in the event that a current above a selected threshold passes through the fuse.

In some examples, in response to the processor receiving sensor signals indicating that the sensor apparatus has incurred an acceleration greater than a selected threshold, the processor is configured to send an emergency alert over the wireless interface notifying a remote device of the acceleration event.

The processor may be configured to send an emergency alert over the wireless interface notifying a remote device of the acceleration event in response to the processor determining that the sensor apparatus has not changed orientation or position over a selected inactivity time interval.

In some examples the processor is configured to determine a battery level of the battery, and operate in at least two modes of operation based on the determined battery level:
- a first mode of operation when the battery level is at or above a selected level; and
- a second mode of operation that consumes less power when the battery level is below a selected level.

The sensor apparatus may comprise a sealed enclosure hosing the sensor electronics. The sensor enclosure may be waterproof to IP 68. In some examples the sensor apparatus comprises a one-way valve permitting air to escape the sensor apparatus when the pressure difference across the one-way valve is above a selected threshold. For example, the one-way valve may comprise a membrane configured to permit the passage of air therethrough but to inhibit the passage of liquid (such as water) therethrough.

In another aspect of the disclosure there is described a sensor apparatus for an item of smart clothing, the sensor apparatus comprising sensor electronics comprising:
- a position and/or orientation sensor coupled to a processor;
- a wireless communications interface coupled to the processor for sending signals indicative of position and/or orientation to a remote device; and
- a battery for powering the processor;

wherein the sensor apparatus comprises a one-way valve permitting air to escape the sensor apparatus when the pressure difference across the one-way valve is above a selected threshold.

In some examples the sensor electronics are coated and/or potted to inhibit the ability of water and/or moisture to access the electronics.

In another aspect of the disclosure there is described a sensor for an item of smart clothing, the sensor comprising an orientation sensor, a processor, and a wireless communications interface, wherein the sensor is configured to communicate with a second sensor via a wireless communications interface;
wherein, based on knowledge of the orientation of the sensor in the x axis, and knowledge of the orientation of the second sensor in the x and y axes, the processor is configured to invert the orientation of the sensor in the y axis so that the orientation in the y axis for the sensor is opposite to the orientation of the second sensor in the y axis.

The sensor may be configured to output the inverted sensor signal in the y axis to a remote device via the wireless communication interface.

DRAWINGS

Embodiments of the disclosure will now be described, by way of example only, with reference to the accompanying drawings, in which.

SPECIFIC DESCRIPTION

Figure 1:
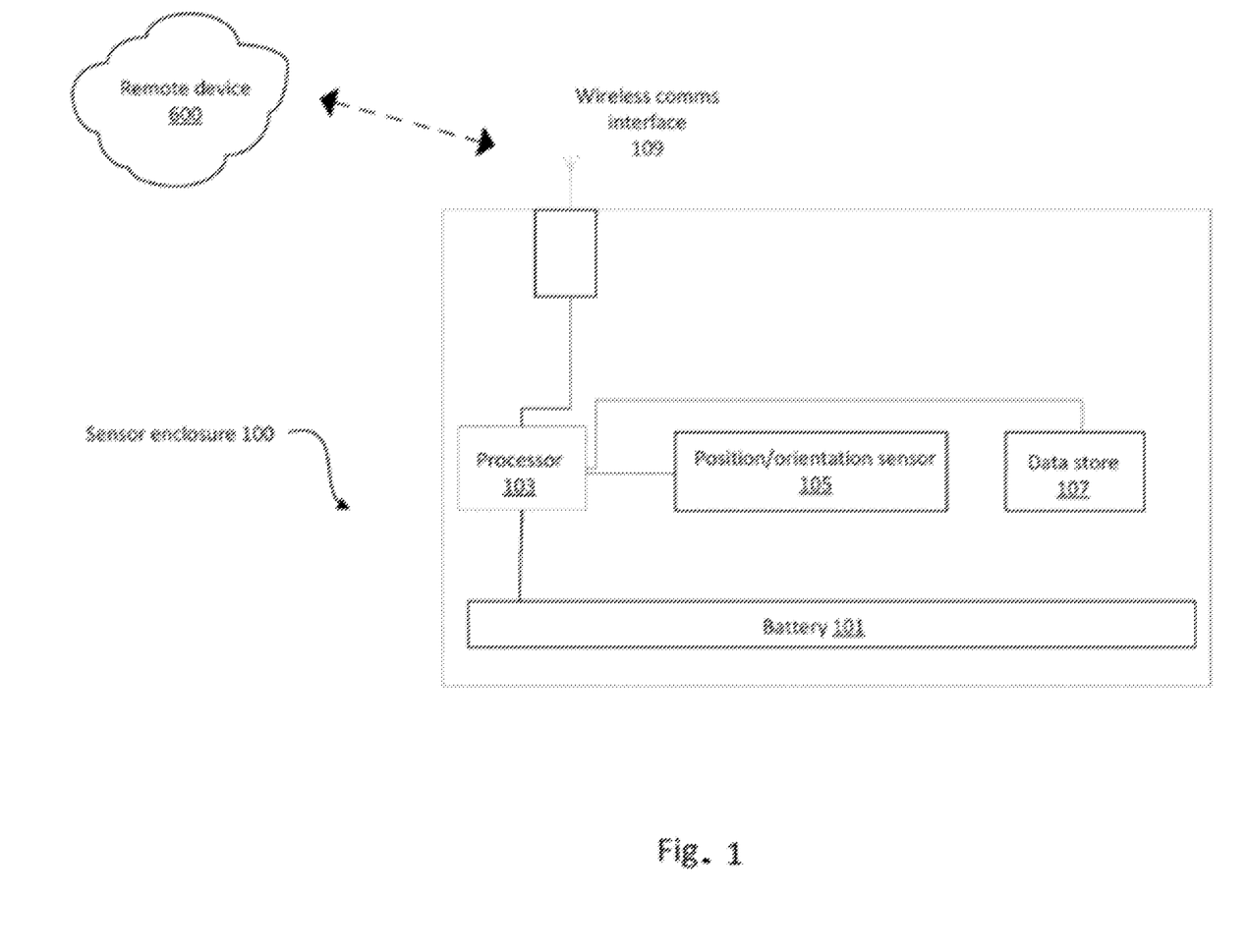
FIG. 1 shows a plan view of an example sensor apparatus for an item of smart clothing.

FIG. 1 shows an example sensor apparatus 100 for an item of smart clothing. The sensor apparatus 100 shown in FIG. 1 comprises an enclosure that houses sensor electronics comprising at least one position and/or orientation sensor 105, a data store 107, a processor 103 and a battery 101. The sensor apparatus 100 shown in FIG. 1 also comprises a wireless communications interface 109. The processor is coupled to the battery 101, the position/orientation sensor 105, the data store 107 and the wireless communications interface 109. The processor 103, at least one position and/or orientation sensor 105, wireless communications interface 109 and data store 107 may be provided on a printed circuit board, PCB, and together with the battery 101, may be called the "sensor electronics".

In some examples the at least one position and/or orientation sensor comprises at least one of a 3-axis accelerometer, a 3-axis gyroscope and a magnetometer.

In some examples the sensor apparatus 100 may be adapted to fit within an item of clothing, such as an item of workwear. For example, the sensor apparatus may have attachment means for attaching the sensor apparatus 100 to the item of clothing. In some cases the attachment means may comprise wings or ribs, for example allowing the wings or ribs to be attached to the item of clothing via stitching. In some examples the sensor apparatus 100 may be adapted to fit within small pockets sewn into the item of clothing. In some examples the sensor apparatus may also comprise external markings, for example indicating an intended direction and/or orientation for incorporation into the item of clothing. For example, the external markings may indicate in which orientation to attach the sensor apparatus 100 to the item of clothing so that a forward direction is known. To fit inside an item of clothing comfortably, the target size for the sensor apparatus 100 is around 50×15×5 mm, which is primarily governed by the size of the battery 101. Preferably the battery 101 provides enough power to operate the sensor apparatus 100 for 12 hours.

Preferably the sensor apparatus 100 is rugged and strong enough to protect the sensor electronics contained inside it. For example, the sensor apparatus 100 may comprise an enclosure housing the sensor electronics that is configured to protect against mechanical damage such as snapping of the PCB, components or wires dragged off the board by abrasion. The enclosure may also be configured to inhibit the risk of short circuits which at its worse could cause the battery terminals to connect potentially starting a fire. The enclosure may also be configured to protect against extremes in temperature. For example, the electronic components have a finite operational and storage temperature range. The battery 101 has the most limited temperature range, which if exceeded could cause mechanical damage, out gassing or even fire. The enclosure may also be configured to inhibit moisture ingress which could result in freezing, causing mechanical damage and/or conductivity changes and altering resistance between components. Accordingly, preferably the sensor electronics and battery 101 are completely enclosed and made water proof to IP68.

The sensor apparatus 100 may protect the sensor electronics by encasement. In addition, the sensor electronics/PCB may be conformally coated which will add another degree of moisture and short circuit protection. In some examples, the sensor apparatus 100 may be encapsulated, comprising some sort of rugged encasement of the complete electronics by a compound. This could also be combined with an enclosure to add another degree of mechanical protection. Preferably the sensor apparatus 100 comprises a full encapsulant combined with a rugged encasement, particularly if the sensor apparatus 100 is designed for placement within a pair of workwear, such as trousers. If the potting compound has a different rate of thermal expansion than the PCB and sensor electronics underneath, then mechanical damage can ensue. Preferably the parts are dipped in a two-part silicone to get a compliant coating before immersing in epoxy. Additionally/alternatively the sensor apparatus 100 may be over-moulded.

The processor 103 is configured to receive signals indicative of a change in position and/or orientation from the at least one position and/or orientation sensor 105. The processor 103 is configured to determine from the received signals whether there has been a change in position and/or orientation of the sensor apparatus 100 over a first selected time interval. In the event that there has been a change in position and/or orientation of the sensor apparatus 100 over the first selected time interval, the processor 103 is configured to record the change in position and/or orientation to the data store 107. The first selected time interval may be selected based on the type of position and/or orientation information being recorded, the size of the data store 107 and/or the capacity of the battery 101.

In the example shown in FIG. 1, the processor 103 comprises a system clock and the processor 103 is configured to record a time based on the system clock when recording a change in position and/or orientation. In the example shown in FIG. 1, the processor 103 is also configured to operate the wireless communications interface 109, and to upload data stored in the data store 107 to a remote device 600 via the wireless communications interface 109. For example, the processor 103 may be configured to determine if the wireless communications interface 109 is coupled to the remote device 600 and in response to determining that the wireless communications interface 109 is coupled to the remote device, upload data stored in the data store 107 to the remote device 600.

In the example shown in FIG. 1, in the event that there has not been a change in position and/or orientation of the sensor apparatus 100 over the first selected time interval, and in some examples no other change in state such as a change in temperature and/or humidity, the processor 103 is configured to record a null or no value to the data store 107.

In the example shown in FIG. 1, the processor 103 is configured to determine if the position and/or orientation of the sensor apparatus 100 is still changing at the end of the first selected time interval, and in the event that the position and/or orientation of the sensor apparatus 100 has stopped changing at the end of the first selected time interval, to record the change in position and/or orientation to the data store 107. In the event that the position and/or orientation of the sensor apparatus 100 is still changing at the end of the first selected time interval, the processor 103 may be configured to record a null or no value to the data store 107.

Recording the change in position and/or orientation may comprise recording the position and/or orientation of the sensor apparatus 100 at the beginning of the first selected time interval and the position and/or orientation of the sensor apparatus 100 at the end of the first selected time interval.

In the example shown in FIG. 1, the processor 103 is configured to record the change in position and/or orientation to the data store 107 in the event that the change in position and/or orientation is above a threshold level of change in position and/or orientation, for example, if the change in orientation of the sensor apparatus 100 is greater than 10 degrees, for example greater than 20 degrees.

In the example shown in FIG. 1, the processor 103 is also configured to receive signals from the at least one position and/or orientation sensor 105 by polling the position and/or orientation sensor 105 repeatedly at a second selected time interval that is shorter than the first selected time interval for determining if there has been a change in position and/or orientation of the sensor apparatus 100.

In some examples, the first and/or second selected time intervals may be selected based on what type of sensor(s) the position and/or orientation sensor 105 is. For example, if the position and/or orientation sensor 105 comprises an accelerometer and/or magnetometer, the second selected time interval may be selected to be relatively short compared to the first selected time interval. However, if the position and/or orientation sensor 105 comprises a gyroscope, the second selected time interval may be selected to be relatively long, for example similar to or the same as the first selected time interval. In some examples, if the position and/or orientation sensor 105 comprises a number of different position and/or orientation sensors, the processor 103 may be configured to poll each respective sensor at a different selected time interval based on what type of sensor it is. The length of the second selected time interval may be selected so as not to miss any important sudden acceleration events that only occur briefly and suddenly.

In operation, the sensor apparatus 100 may be incorporated into a user's item of clothing and record sensor measurements based on the user's movements. The processor 103 polls the at least one position and/or orientation sensor 105 for position and/or orientation information at a selected frequency corresponding to the second selected time interval. The processor 103 compares this polled position and/or orientation information from the beginning of the first selected time interval with position and/or orientation information from the end of the first selected time interval, and at any recorded time points within the first selected time interval.

In the example shown in FIG. 1, because the processor 103 polls the at least one position and/or orientation sensor a number of times within the first selected time interval (because it polls the position and/or orientation sensor 105 at a second selected time interval that is shorter than the first selected time interval), the processor 103 may compare the position and/or orientation information from a plurality of discrete time points within the first selected time interval to determine if there has been a change in position and/or orientation (for example, if there as a sudden drop/acceleration event that may be shorter than the first selected time interval) over the first selected time interval.

If there has been a change in position and/or orientation of the sensor apparatus 100 at any point within that first selected time interval, and that change is greater than a selected threshold level of change (selected so as to remove any unwanted noise/minor fluctuations that would be normal if the sensor apparatus 101 were incorporated into an item of clothing worn by a user) the processor 103 is configured to record that change in position and/or orientation to the data store 107 along with a time stamp based on time information obtained from the system clock. If there has not been a change in position and/or orientation over the first selected time interval, or it is not greater than the selected threshold level of change, the processor 103 is configured to record a null or no value to the data store 107. This may reduce the amount of data storage required and also the amount of data that ultimately needs to be uploaded to a remote device 600 via the wireless communications interface 109, which in turn may reduce the power consumption of the battery 101.

At the end of the day, for example when a user returns home, the wireless communications interface 109 comes into range of user's wireless connection and connects to a remote device 600. The processor 103 detects that the wireless communications interface 109 is connected to a remote device 600, and in response to determining that the wireless communications interface 109 is coupled to the remote device, it uploads time-stamped data stored in the data store 107 to the remote device 600.

In some examples, the processor 103 is configured to operate the wireless communications 109 interface to communicate with the wireless communications interface of another sensor apparatus. For examples, the processor 103 may be configured to receive signals indicative of a change in position and/or orientation from at least one position and/or orientation sensor from the other sensor apparatus and to determine the position and/or orientation of the other sensor apparatus. The processor 103 may be configured to compare the position and/or orientation of the other sensor apparatus with its own position and/or orientation.

The comparison may be used to determine relative movement of at least a portion of a user's anatomy. For example, one sensor apparatus 100 may be attached to an item of clothing to one side of a user's joint (for example, below the knee) and another sensor apparatus 100 may be attached to the item of clothing to the other side of the user's joint (for example, above the knee) and the comparison between the position and/or orientation of the two sensors apparatus 100 used to determine the degree of bend of the user's joint. In some examples, an item of "smart" clothing may contain a plurality of sensor apparatus 100. For example, a pair of "smart" trousers may comprise two sensor apparatus 100 on each leg, one below the knee and one above the knee on each leg to detect if a user is bending their legs, for example if they are working in a kneeling position. In addition, a pair of "smart" trousers may comprise a sensor apparatus 100 on the waist of the trousers, for example to detect if the user is twisting or leaning.

In some examples the processor 103 is configured to determine whether there has been a change in position and/or orientation of the other sensor apparatus with respect to the sensor over a third selected time interval. In the event that there has been a change in position and/or orientation of the other sensor apparatus over the third selected time interval, the processor is configured to record the change in position and/or orientation of the other sensor apparatus to the data store 107.

In some examples the processor 103 may be configured to transmit data obtained from the at least one position/orientation sensor 105 on a regular basis to a remote device 600 (such as a user's mobile phone and/or a server, such as a cloud-based server), using the wireless communications interface 109, and a wireless communications protocol such as Bluetooth® LE V4.2 or above. An example Bluetooth® LE range may be in the order of 100 m in an open field environment, and a minimum collection time of the position/orientation data may be 1 Hz.

If there is no connection to a remote device (such as a mobile phone or cloud-based server) via the wireless communications interface 109, data may be time tagged and stored locally (for example on data store 107) until the link is available again and the historical data uploaded.

It will be understood, however, that in some examples the processor 103 is not configured to determine from the received signals whether there has been a change in position and/or orientation of the sensor apparatus 100 over a first selected time interval. For example, the processor 103 may simply record all data received from the at least one position and/or orientation sensor 105 to the data store 107.

In some examples, the processor 103 is configured to determine if the wireless communications interface 109 is coupled to a remote device 600 and in response to determining that the wireless communications interface 109 is coupled to the remote device, upload data to the remote device. The processor 103 may be configured to adjust the data (for example, time tagged data as discussed above) uploaded to the remote device 600 based on at least one of (i) an analysis of the data stored on the data store 107 and (ii) a parameter of the connection with the remote device 600 via the wireless communications interface 109.

The analysis performed by the processor 103 may comprise determining if the data can be compressed, or if the volume of data can be reduced. For example, the processor 103 may be configured to remove data values where there has been no change in position and/or orientation, or only a change in positions and/or orientation below a selected threshold level.

The parameter of the connection with the remote device 600 may comprise at least one of the bandwidth of the connection with the remote device 600, and the battery level of the battery 101 in the sensor apparatus 100. For example, if the bandwidth is low (for example, below a selected threshold) the processor 103 may be configured to send less data to the remote device 600. Similarly, if the battery level is low (for example below a selected threshold) the processor 103 may be configured to send less data to the remote device 600. The remote device 600 may be based on the cloud (for example provided as a means of internee/web-based storage). The connection with the remote device 600 may be direct, for example the sensor may connect directly to a wide area network such as the internet via the wireless communications interface, or it may be indirect, for example the sensor apparatus 100 may connect to a user's mobile phone via the wireless communications interface 109, which in turn may connect to a wide area network such as the internet to connect to a remote device 600, such as the cloud.

Figure 2:
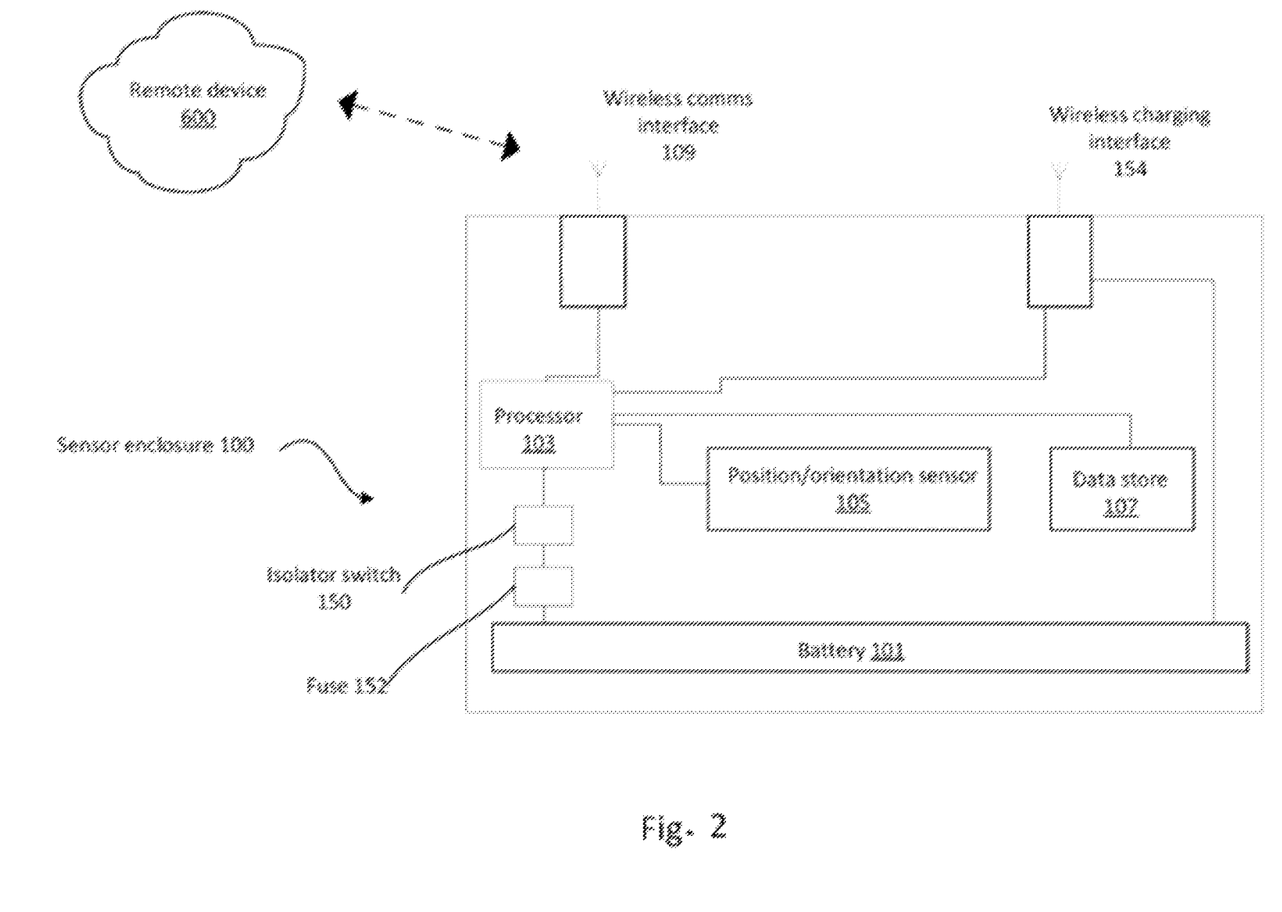
FIG. 2 shows a plan view of another example sensor apparatus for an item of smart clothing.

FIG. 2 shows another example sensor apparatus 100. The sensor apparatus 100 of FIG. 2 is in many respects similar to the sensor apparatus 100 of FIG. 1, and may share features and/or functionality with the sensor apparatus 100 described above and as shown in FIG. 1.

In the example shown in FIG. 2, the sensor apparatus 100 comprises a wireless charging interface 154 coupled to the processor 103 and the battery 101. The wireless charging interface 154 is configured to receive a charging current from a remote charging station. The wireless charging interface 154 may be configured to receive radio frequency, RF, energy for charging the battery 101.

In the example shown in FIG. 2, the processor 103 is configured to determine if the battery 101 is being charged via the wireless charging interface 154, and in response to determining that the battery is being charged via the wireless charging interface 154, upload data stored in the data store 107 to the remote device 600 via the wireless communications interface 109. The processor 103 may determine if the battery 101 is being charged via the wireless charging interface 154 by detecting if a current is flowing through the wireless charging interface 154, for example if a current is being induced in the wireless charging interface 154. Additionally or alternatively the sensor apparatus 100 may further comprise a battery charge sensor coupled to the battery 101, wireless charging interface 154 and/or the processor 103, and the battery charge sensor may be configured to detect if a charge current is present and send a signal to the processor 103.

In some examples the processor 103 comprises a system clock, and the processor is configured to synchronise the system clock to a time signal received from a remote charging station via the wireless communications interface 154. The system clock may be used to time stamp data recorded to the data store. By synchronising the system clock to a time signal received from a remote charging station, if a number of sensor apparatus 100 are being used at the same time in the same item of smart clothing (for example for comparative analysis of movement of a user's anatomy, for example for determining the degree of bend of a user's joint), direct and accurate comparison with sensor data obtained from different sensor apparatus 100 may be performed.

In some examples the processor 103 is shared with at least one of the wireless communications interface 109 and the wireless charging interface 154. There are a number of factors requiring consideration in the selection of the processor 103, and this is closely tied in with the selected solution for the Bluetooth® LE provider. Most of the Bluetooth® LE solutions have an on-board Arm® Cortex processor that is used to control the real-time Bluetooth® interactions. Bluetooth® processors also typically have some limited hardware Io functionality which includes digital IO pins, SPI and I2C interfaces. Ideally, we would want this to be the only processor on the circuit board to minimise component counter and hence power consumption. However, both the Bluetooth® and the application components of the sensor's firmware require a real time component, which makes the division of labour between the Bluetooth® and application difficult. To overcome this limitation it is proposed to have a processor 103 running the application and then a Bluetooth® processor running just the wireless communications interface 109 allowing each to dedicate 100% of their focus to their relevant applications.

The processor 103 may have firmware running on it that is dedicated and bespoke to the system. In some examples the processor 103 may be configured to perform the following functionality:

Keep the sensor electronics (such as the wireless communications interface 109, at least one position and/or orientation sensor 105) running on as low power as possible to preserve battery life;

Read the at least one position and/or orientation sensor 105 on a regular basis (for example by polling the at least one position and/or orientation sensor 105), filtering any unwanted movements and at least once per second calculate the angle of the sensor apparatus 100 in respect to the ground;

Read the temperature and battery state at least once per minute;

Store the angles, temperature and battery states in a time tagged ring buffer datalog (for example on data store 107);

The datalog (for example the data store 107) may be non-volatile and have sufficient capacity to last and record 12 hours of position and/or orientation data;

Control the wireless communications interface 109, such as a Bluetooth® LE V4.2 interface over which a remote device 600 such as a charging station and/or a user's mobile phone may communicate with the sensor apparatus 100;

Offload the contents of the datalog (for example stored on data store 107) when requested, for example to a remote device 600 via the wireless communications interface 109;

Be able to update the firmware operating on the processor 103 wirelessly via the wireless communications interface 109 (for example over Bluetooth®) from a remote device 600 such as a user's mobile phone and/or charging station;

Be able to report the current configurations and IDs of the sensor electronics over the wireless communications link via the wireless communications interface 109;

Run and report any self-test or error logs over the wireless communications link via the wireless communications interface 109.

The wireless communications interface 109 may be any Bluetooth® device, such as Bluetooth® LE, for example that implements V4.0 or above, for example V4.2 or above of the Bluetooth® LE specification.

The battery 101 may be a Li-Ion battery as typically these provide the highest charge density vs cost of any of the currently available battery technologies. The charge capacity in terms of mAh governs the physical size of the battery. This mAh rating is driven by the current consumption of the other electronic components, which in-turn is driven by the update rate of the position/orientation data and of the transmission of this data via the wireless communications interface 109 back to a remote device 600 such as a mobile phone and/or cloud-based server. The most power-hungry aspect is the wireless (such as Bluetooth® LE) data transmission via the wireless communications interface 109, which is governed by the range requirement, the data bandwidth required and update frequency. Preferably the mAh rating is targeted at a 70 mAh battery, although 100 mAh are available but are around 20% bigger. Batteries of this size are very similar to the size of the PCB.

Preferably the sensor electronics are completely sealed in a waterproof (rated to IP68) enclosure. In such examples there will not be any connectors available to introduce power to charge the battery. Accordingly, the battery 101 may be charged via a wireless charging interface 154 as shown in FIG. 2. This may allow charge to be conveyed via radio frequency, RF, energy, allowing a group of sensors to be charged simultaneously within a Faraday Cage defined apparatus. A limit on the amount of power available using this system may be around 15 mA, which using the 0.20 charge requirement of most Li-Ion batteries to place the battery charge around the 75 mAh range, which confirms the battery sizing listed above. To receive the power by RF a certain amount of circuit board space may have to be reserved to allow the placement of an antenna for the battery charging system. This antenna may be required to have a two dimensional, or even a three dimensional component to allow charging in any orientation.

Figure 4:
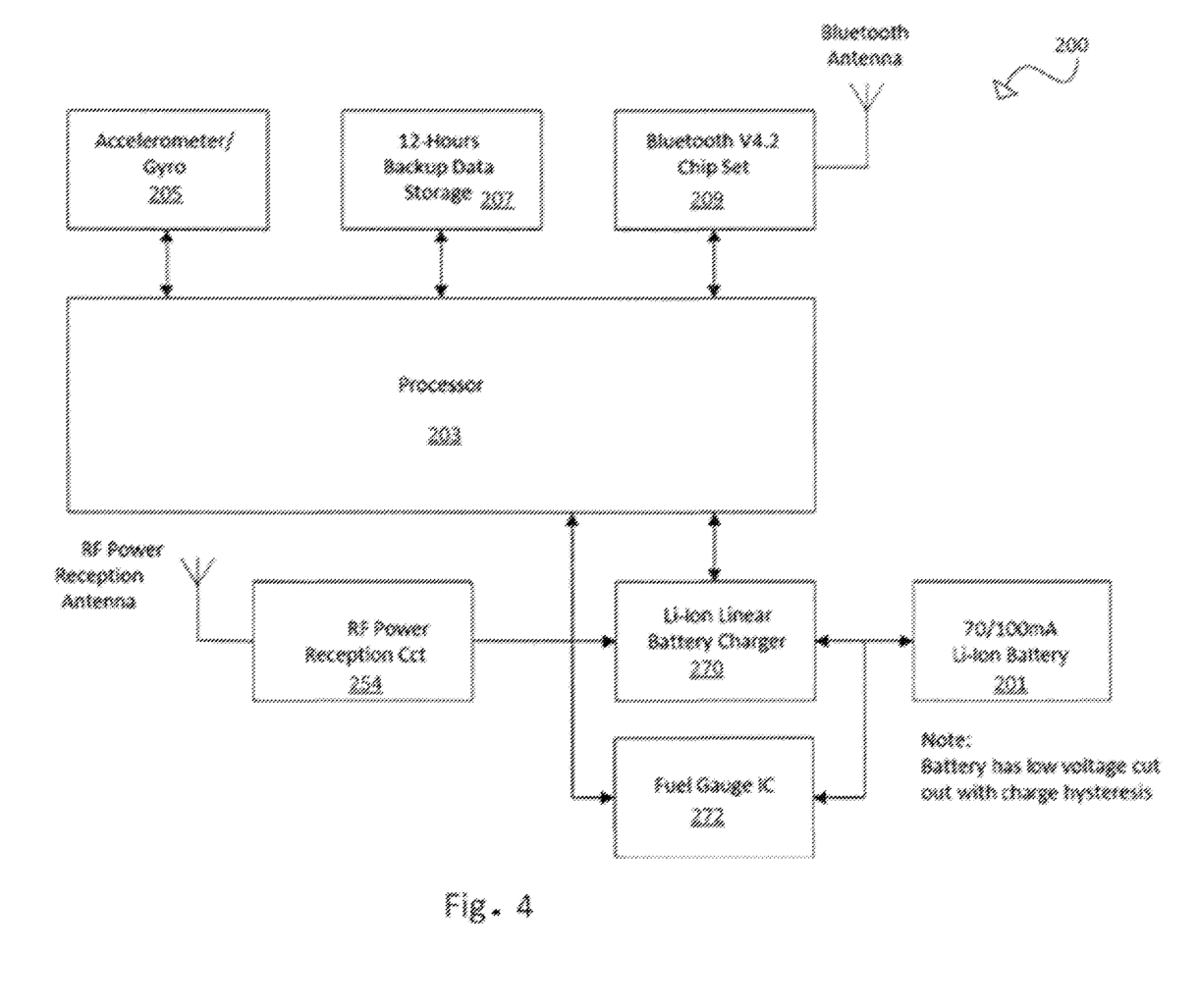
FIG. 4 shows a plan view of another example sensor apparatus for an item of smart clothing.

Once the power has been received and rectified then in some examples a Li-Ion Battery charger IC may be required 270 (as shown in FIG. 4 and described in more detail below) to regulate and control the charging process. There are a number of different IC's available from a range of manufacturers that could be used for this purpose, for example an STNS01 IC.

In some examples the position/orientation sensor 105 may include an ST LSM6DSL Inertial Module which includes a 3-Axis±16 g accelerometer and a 3-Axis gyroscope that is accessed via SPI/I2C.

The data store 107 may be configured to provide a back-up memory. The back-up memory may store angle information when the user's mobile phone is not available or in range, for onward transmission when it does become available. There are a number of technologies available that could be used, and they may be accessed via an SPI/I2C interface. The size of the memory is driven by the amount of time stamped data the sensor can collect in a 12-hour period, which is the target operational time from a single charge. At minimum, assuming one position/orientation reading every second, a memory size of 128 kbytes will be required. In addition to the position/orientation, battery and temperature information may also be recorded. Preferably a non-volatile memory around the 2M byte mark will be more appropriate.

In some examples the sensor apparatus 100 also comprises a temperature and/or humidity sensor (not shown) coupled to the processor 103. In some examples the temperature sensor may be integrated into the position/orientation sensor 105. The temperature of the sensor apparatus 100 may be monitored to ensure it is kept within a safe operating range and the user can be notified, for example via a notification message sent to a remote device (such as a mobile phone) via the wireless communications interface 109, if selected limits are being reached.

For example, the processor 103 may be configured to determine and record temperature and/or humidity data to the data store 107 based on signals received from the at least one of a temperature sensor and a humidity sensor. The processor 103 may be configured to record temperature and/or humidity data to the data store 107 when the processor 103 records the change in position and/or orientation to the data store 107. However, in other examples, the temperature/humidity data may be recorded less frequently than the position and/or orientation data. For example, the position and/or orientation data may be recorded once a second whereas the temperature and/or humidity data may be recorded once a minute.

In some examples the processor 103 is configured to send an alert via the wireless communications interface 109 in the event that the determined temperature and/or humidity are above a selected threshold. The alert may be sent over a broadcast channel, for example over a Bluetooth® broadcast channel, so that any devices within range receive the alert. In some examples the alert may be configured to operate "smart" or "connected" equipment. For example, the alert message may be configured to turn off a connected washing machine or tumble drier that the sensor apparatus 100 may have inadvertently been placed inside.

The processor 103 may be configured to determine a rate of increase in temperature and/or humidity, and to send an alert via the wireless communications interface 109 in the event that the determined rate of increase in temperature and/or humidity are above a selected threshold rate of increase.

The Aviation Authority requires that the when Li-Ion batteries are transported by air, that the batteries are isolated from the equipment and that no wireless transmissions take place.

Accordingly, in some examples the processor 109 may be configured to receive signals, such as instruction signals, via the wireless communications interface 109. The signals may originate from a bespoke application operating on a remote device 600 coupled to the sensor apparatus 100 via the wireless communications interface 109. In response to a signal received via the wireless interface 109, the processor 103 may be configured to disconnect the at least one position and/or orientation sensor 105 from the battery 101 and to reduce the battery level below a selected level of charge. For example, the selected level of charge may be 25% or less of fully charged. In some examples the processor may be configured to fully isolate the sensor electronics from the battery 101 (for example by operation of an isolator switch 150 described below with reference to FIG. 3) and to ensure flight safe mode. This will allow the sensor apparatus 100 to be safely shipped from the factory and also for a user to ship it by air.

Figure 3:
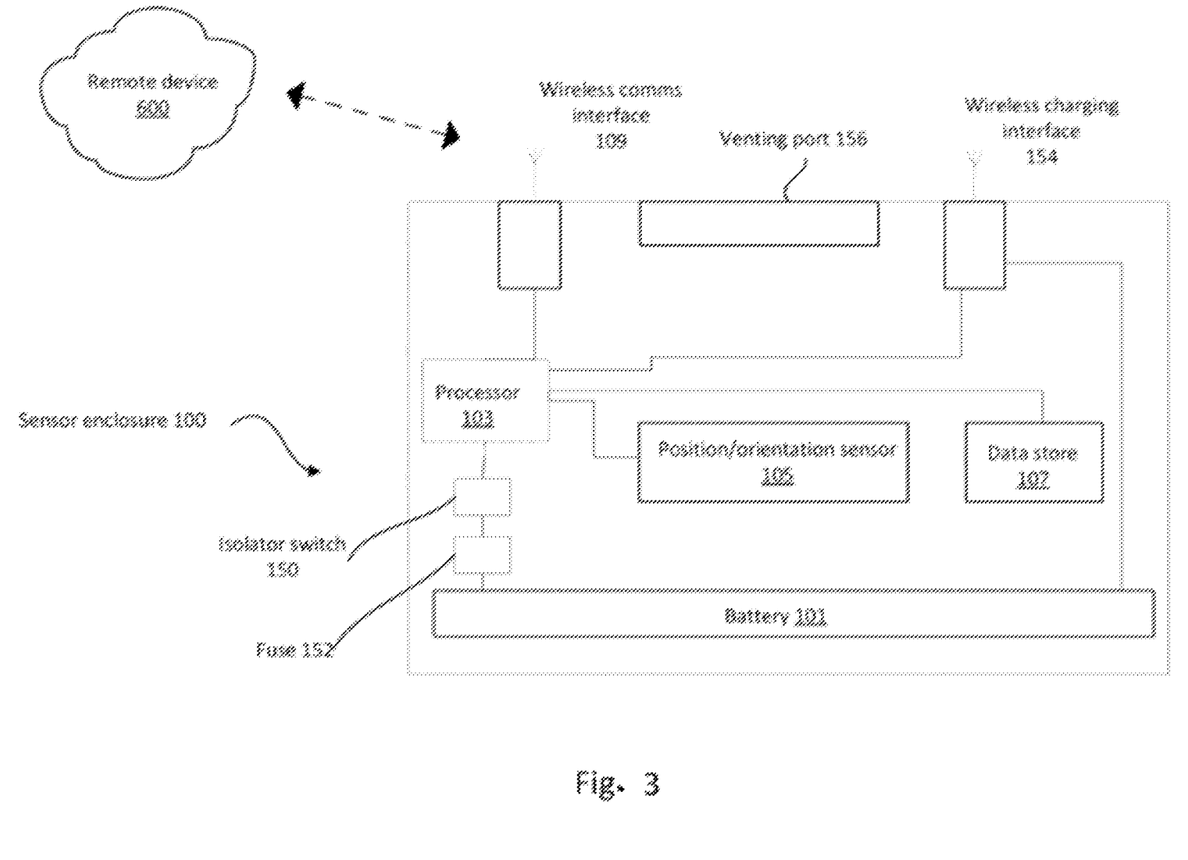
FIG. 3 shows a plan view of another example sensor apparatus for an item of smart clothing.

FIG. 3 shows another example sensor apparatus 100. The sensor apparatus 100 of FIG. 3 is in many respects similar to the sensor apparatus 100 of FIG. 1 and FIG. 2, and may share features and/or functionality with the sensor apparatus 100 described above and as shown in FIGS. 1 and 2.

In the example shown in FIG. 3, the sensor apparatus 100 further comprises an isolator switch 150 connected in series between the battery 101 and the processor 103. In response to receiving an isolate signal via the wireless communications interface 109 (for example, from remote device 600), the processor 103 is configured to operate the isolator switch 150 to disconnect the battery 101 from at least some of, for example all of, the sensor electronics. This may include any or all of the processor 103, the at least one position and/or orientation sensor 105, the data store 107, the wireless charging interface 154 and the wireless communications interface 109.

In the example shown in FIG. 3 the processor 103 is configured to determine if the battery 101 is being charged via the wireless charging interface 154, and in response to determining that the battery 101 is being charged via the wireless charging interface 154, the processor 103 is configured to operate the isolator switch 150 to connect the battery 101 to at least some of the sensor electronics, such as the position and/or orientation sensor and the wireless communications interface 109. In some examples the processor 103 can set a flag to keep the isolator switch turned on so.

The example shown in FIG. 3 also comprises a fuse 152 connected in series between the battery 101 and the isolator switch 150. The fuse 152 is configured to blow in the event that a current above a selected threshold passes through the fuse 152.

In the example shown in FIG. 3, in response to the processor 103 receiving sensor signals indicating that the sensor apparatus 100 has incurred an acceleration greater than a selected threshold, the processor 103 is configured to send an emergency alert over the wireless communications interface 109 notifying a remote device 600 of the acceleration event. For example, the acceleration event may be that a user has fallen suddenly and therefore incurred a sudden acceleration event. Sending an emergency alert may allow a responder to come to the assistance of the user. In some examples the processor 103 is configured to send an emergency alert over the wireless communications interface 109 notifying a remote device of the acceleration event in response to the processor 103 determining that the sensor apparatus 100 has not changed orientation or position over a selected inactivity time interval. For example, if a user is unconscious and/or lying on the floor inactive, the processor 103 may determine that the user is inactive and in need of assistance, and in response to this determination, the processor 103 may be configured to send an emergency alert over the wireless communications interface 109 to allow a responder to come to the assistance of the user.

In the example shown in FIG. 3, the sensor apparatus 100 also comprises a venting port 156 for releasing pressure above a selected threshold from inside the sensor apparatus 100, and thereby reducing the likelihood of the sensor apparatus exploding in the event of failure. In the example shown, the venting port 156 comprises a one-way valve permitting air to escape the sensor apparatus 100 when the pressure difference across the one-way valve is above a selected threshold. The venting port shown in FIG. 3 also comprises a membrane, permitting the escape of air and moisture out of the sensor apparatus 100, but inhibiting the ingress of moisture into the sensor apparatus 100.

In some examples, the position and/or orientation sensor may comprise a GPS sensor. To give the recorded position and/or orientation data context, the processor 103 may also be configured to record GPS positions with the position and/or orientation data.

FIG. 4 shows another example sensor apparatus 200. The sensor apparatus 100 of FIG. 4 is in many respects similar to the sensor apparatus 100 of FIGS. 1, 2 and 3, and may share features and/or functionality with the sensor apparatus 100 described above and as shown in FIGS. 1, 2 and 3.

The sensor apparatus 200 of FIG. 4 comprises a wireless charging interface 254 (in this case an RF charging interface) coupled to a processor 203 and a battery 201 (in this case a 70/100 mA Li-ion battery) via a battery charger 270. Also coupled to the battery 201 and the processor 203 in parallel to the battery charger 270 is a battery fuel gauge 272.

As with the examples described above and as shown in FIGS. 1 to 3, the sensor apparatus 200 comprises a position and/or orientation sensor 205 (in this case an accelerometer and a gyroscope) coupled to the processor 203, a data store 207 coupled to the processor 203, and a wireless communications interface 209 (in this case a Bluetooth® v4.2 chipset) also coupled to the processor 203.

The battery charger 270 may be configured to rectify a charging current received from the wireless charging interface 254 before passing the rectified current to the battery 261. The battery charger 270 may be configured to regulate and control the charging process. There are a number of different IC's available from a range of manufacturers that could be used for this purpose, for example an STNS01 IC.

The battery fuel gauge 272 is configured to determine the battery state of charge. In some examples, this may be performed by simply reading the voltage of the battery 101. However, in some examples the battery fuel gauge 272 may be configured to "coulomb count" to determine the current flowing to and/or from the battery 201 to determine the state of charge of the battery 201. For example, the battery fuel gauge 272 may be an STC3115 IC. The processor 203 may be configured to transmit the battery state of charge information to a remote device 600 via the wireless communications interface 209. For example, the processor 203 may be configured to send an alert to the user (for example by sending a message to the remote device 600) if the battery state becomes low (for example below a selected threshold).

In some examples, the processor 203 is configured to determine a battery level of the battery 201, and operate in at least two modes of operation based on the determined battery level. For example, the processor 203 may be configured to operate in a first mode of operation when the battery level is at or above a selected level, and operate in a second mode of operation that consumes less power when the battery level is below a selected level.

In some examples, the processor 103 is configured to determine in which orientation it coupled to an item of clothing in. For example, the sensor apparatus 100 may comprise external markings indicating a direction of orientation in which the sensor apparatus 100 should be attached in (for example, an arrow may indicate that the sensor apparatus 100 should face in a particular direction). However, the orientation sensor may not know which way is the correct way up. This is because the same sensor apparatus 100 may be used in different parts of the item of clothing, for example for different parts of a user's anatomy. For example, one sensor apparatus 100 may be used for a left leg and one sensor apparatus 100 may be used for a right leg. However, if the same sensor apparatus 100 is used for both positions, and if both sensor apparatus have the same external markings, then one sensor apparatus 100 will be upside-down relative to the other sensor apparatus 100.

To address this problem, the processor 103 of one sensor apparatus 100 (for example, a sensor apparatus 100 attached to a left leg) may communicate with another sensor apparatus 100 (for example, a sensor apparatus 100 attached to a right leg), and based on knowledge of the orientation of the sensor apparatus 100 in the x axis, and knowledge of the orientation of the other sensor apparatus 100 in the x and y axes, the processor 103 may be configured to invert the orientation of the sensor apparatus 100 in the y axis so that the orientation in the y axis for the sensor apparatus 100 (of the left leg) is opposite to the orientation of the other sensor apparatus 100 (of the right leg) in the y axis. In this way, the processor 103 can usefully output correct orientation information, for example to a remote device 600 via the wireless communication interface 109.

In the context of the present disclosure other examples and variations of the apparatus and methods described herein will be apparent to a person of skill in the art.

The invention claimed is:

1. A sensor apparatus for an item of smart clothing, the sensor apparatus comprising sensor electronics comprising at least one position and/or orientation sensor, and a data store, coupled to a processor and powered by a battery;

wherein the processor is configured to receive signals indicative of a change in position and/or orientation from the at least one position and/or orientation sensor;

wherein the processor is configured to determine from the received signals whether there has been a change in position and/or orientation of the sensor apparatus over a first selected time interval; and in the event that there has been a change in position and/or orientation of the sensor apparatus over the first selected time interval, the processor is configured to record the change in position and/or orientation to the data store, wherein the processor is coupled to and configured to operate a wireless communications interface, and wherein the processor is configured to upload data stored in the data store to a remote device via the wireless communications interface, and wherein the sensor apparatus comprises a wireless charging interface for wirelessly charging the battery, and wherein the processor is configured to determine if the battery is being charged via the wireless charging interface, and in response to determining that the battery is being charged via the wireless charging interface, upload data stored in the data store to the remote device via the wireless communications interface.

2. The sensor apparatus of claim 1 wherein, in the event that there has not been a change in position and/or orientation of the sensor apparatus over the first selected time interval, the processor is configured to record a null or no value to the data store.

3. The sensor apparatus of claim 1 wherein the processor is configured to determine if the position and/or orientation of the sensor apparatus is still changing at the end of the first selected time interval, and in the event that the position and/or orientation of the sensor apparatus has stopped changing at the end of the first selected time interval, to record the change in position and/or orientation to the data store.

4. The sensor apparatus of claim 3, wherein in the event that the position and/or orientation of the sensor apparatus is still changing at the end of the first selected time interval, the processor is configured to record a null or no value to the data store.

5. The sensor apparatus of claim 1 wherein recording the change in position and/or orientation comprises recording the position and/or orientation of the sensor apparatus at the beginning of the first selected time interval and the position and/or orientation of the sensor apparatus at the end of the first selected time interval.

6. The sensor apparatus of claim 1 wherein the processor is configured to record the change in position and/or orientation to the data store in the event that the change in position and/or orientation is above a threshold level of change in position and/or orientation.

7. The sensor apparatus of claim 1 wherein the processor is configured to receive signals from the at least one position and/or orientation sensor by polling the position and/or orientation sensor repeatedly at a second selected time interval that is shorter than the first selected time interval for determining if there has been a change in position and/or orientation of the sensor apparatus.

8. The sensor apparatus of any claim 1 wherein the processor comprises a system clock and wherein the processor is configured to record a time based on the system clock when recording a change in position and/or orientation.

9. The sensor apparatus of claim 1 wherein the processor is configured to determine if the wireless communications interface is coupled to the remote device and in response to determining that the wireless communications interface is coupled to the remote device, upload data stored in the data store to the remote device.

10. The sensor apparatus of claim 1 wherein the processor comprises a system clock and wherein the processor is configured to record a time based on the system clock when recording a change in position and/or orientation; and wherein the charging interface is configured to receive a charging current from a remote charging station via the wireless charging interface, and wherein the processor is configured to synchronise the system clock to a time signal received from the remote charging station via the wireless communications interface.

11. A sensor apparatus for an item of smart clothing, the sensor apparatus comprising sensor electronics comprising at least one position and/or orientation sensor, and a data store, coupled to a processor and powered by a battery;

wherein the processor is configured to receive signals indicative of a change in position and/or orientation from the at least one position and/or orientation sensor;

wherein the processor is configured to determine from the received signals whether there has been a change in position and/or orientation of the sensor apparatus over a first selected time interval; and in the event that there has been a change in position and/or orientation of the sensor apparatus over the first selected time interval, the processor is configured to record the change in position and/or orientation to the data store, wherein the processor is coupled to and configured to operate a wireless communications interface, and wherein the processor is configured to upload data stored in the data store to a remote device via the wireless communications interface, and wherein the processor is configured to operate the wireless communications interface to communicate with the wireless communications interface of another sensor apparatus, and to receive signals indicative of a change in position and/or orientation from at least one position and/or orientation sensor from the other sensor apparatus and to determine the position and/or orientation of the other sensor apparatus, and compare the position and/or orientation of the other sensor apparatus with its own position and/or orientation.

12. The sensor apparatus of claim 11 wherein the processor is configured to determine whether there has been a change in position and/or orientation of the other sensor apparatus with respect to the sensor over a third selected time interval; and in the event that there has been a change in position and/or orientation of the other sensor apparatus over the third selected time interval, the processor is configured to record the change in position and/or orientation of the other sensor apparatus to the data store.

13. A sensor for an item of smart clothing, the sensor comprising an orientation sensor, a processor, and a wireless communications interface, wherein the sensor is configured to communicate with a second sensor via a wireless communications interface;

wherein, based on knowledge of the orientation of the sensor in the x axis, and knowledge of the orientation of the second sensor in the x and y axes, the processor is configured to invert the orientation of the sensor in the y axis so that the orientation in the y axis for the sensor is opposite to the orientation of the second sensor in the y axis.

14. The sensor of claim 13 wherein the processor is configured to output the inverted sensor signal in the y axis to a remote device via the wireless communication interface.

\* \* \* \* \*